United States Patent [19]

Shinnaka et al.

[11] Patent Number: 4,906,411
[45] Date of Patent: Mar. 6, 1990

[54] PROCESS FOR PRODUCING 2-METHYL-1,4-NAPHTHOQUINONE

[75] Inventors: Atsushi Shinnaka; Yukio Narabu, both of Ibaraki, Japan

[73] Assignee: Eisai Chemical Co., Ltd., Ibaraki, Japan

[21] Appl. No.: 51,380

[22] Filed: May 19, 1987

[30] Foreign Application Priority Data

May 21, 1986 [JP] Japan ................................ 61-114794

[51] Int. Cl.[4] ...................... C07C 46/02; C07C 46/04; C07C 50/12
[52] U.S. Cl. .................................................... 552/299
[58] Field of Search .................................... 260/396 R

[56] References Cited

U.S. PATENT DOCUMENTS 4,482,493 11/1984 Matsumoto et al. ............ 260/396 R
4,632,782 12/1986 Komatsu et al. ............... 260/396 R

FOREIGN PATENT DOCUMENTS 239433 11/1985 Japan ............................. 260/396 R Primary Examiner—Vivian Garner
Attorney, Agent, or Firm—Wenderoth, Lind & Ponack

[57] ABSTRACT

An improved process for producing 2-methyl-1,4-naphthoquinone with a high yield comprising reaction of a 1-lower-alkoxy-2-methyl naphthalene with hydrogen peroxide in the presence of a hexacyanoferric acid or a salt thereof as catalyst. This process does not employ hazardous chromium compounds unlike conventional methods.

6 Claims, No Drawings

PROCESS FOR PRODUCING 2-METHYL-1,4-NAPHTHOQUINONE

BACKGROUND OF THE INVENTION

1. Field of the Invention

This invention relates to an improved process for producing 2-methyl-1,4-naphthoquinone (menadione, vitamin $K_3$). More particularly, it relates to a process for producing 2-methyl-1,4-naphthoquinone which comprises reaction of a 1-lower-alkoxy-2-methylnaphthalene with hydrogen peroxide in the presence of a hexacyanoferric acid or a salt thereof as catalyst.

2. Description of the Prior Art

A method is known for producing 2-methyl-1,4-naphthoquinone, in which 2-methylnaphthalene is oxidized with chromium trioxide [P. P. T. Sah, Rec. Trav. Chim., 59, 1021 (1940)]. An improvement thereto was also proposed, in which a special apparatus called "film-reactor" is used to prevent excessive oxidation by chromium trioxide [H. Veldstra and P. W. Wiardi, Rec. Trav. Chim, 62, 75 (1943)]. These methods are not satisfactory for commercial production because chromium trioxide (a substance which can be an environmental harzard) is used and the product yield is rather low (29% for the former, and 45% for the latter).

DETAILED DESCRIPTION OF THE INVENTION

Studies aimed at developing a simple process free from the above-mentioned disadvantages and capable of producing 2-methyl-1,4naphthoquinone with a high yield on a commercial basis have led us to find that this object can be achieved if a 1-lower-alkoxy-2-methyl-naphthalene, a material which is readily available on a commercial basis, is allowed to react with hydrogen peroxide in the presence of an oxidation catalyst. This invention was accomplished based on these findings.

Thus, this invention relates to a process for producing 2-methyl-1,4-naphthoquinone which comprises reaction of a 1-lower-alkoxy-2-methylnaphthalene with hydrogen peroxide in the presence of a hexacyanoferric acid or a salt thereof as catalyst.

As examples of the 1-lower-alkoxy-2-methylnapthalene used as the starting material in the process of this invention, there may be mentioned, among others, 1-methoxy-2-methylnaphthalene, 1-ethoxy-2-methylnaphthalene and 1-propoxy-2-methylnaphthalene.

Typical examples of the hexacyanoferric acid or salt thereof to be used as the catalyst include the following:

hexacyanoferric acid such as hexacyanoferric acid (II), hexacyanoferric acid (III), etc.;

an alkali metal hexacyanoferrate such as potassium hexacyanoferrate (III) [potassium ferricyanide], potassium hexacyanoferrate (II) [potassium ferrocyanide], sodium hexacyanoferrate (III), sodium hexacyanoferrate (II), etc.; and ammonium hexacyanoferrate such as ammonium hexacyanoferrate (III), ammonium hexacyanoferrate (II), etc.

The suitable amount of this catalyst is 0.1 to 10.0%, based on the weight of 1-lower-alkoxy-2-methylnaphthalene used, most preferably about 1 to 5%.

The reaction is carried out by adding hydrogen peroxide to a solution of a 1-lower-alkoxy-2-methylnaphthalene and an alkali metal hexacyanoferrate, for example, in a solvent, such as glacial acetic acid and aqueous acetic acid. This reaction proceeds at temperatures in the range from 20° to 100° C. But, since the reaction rate is too slow at temperatures lower than 20° C. and tarry products tend to be formed at temperatures higher than 80° C., the reaction should preferably be conducted at a temperature in the range from 40° to 80° C., most preferably from 50° to 60° C.

The following Examples will further illustrate the invention.

EXAMPLE 1

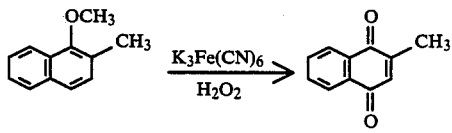

In a four-necked, round-bottomed flask fitted with a stirrer, a thermometer, a cooler and a dropping funnel, were placed 0.5 g of potassium ferricyanide, 17.2 g of 1-methoxy-2-methylnaphthalene (90% content), 10 ml of water and 100 ml of glacial acetic acid. The mixture was heated with stirring, and dropping of 35% hydrogen peroxide was started when the internal temperature reached 55° C., with the total amount (33 g) being added over a period of one hour. Stirring was further continued for four hours while maintaining the internal temperature within the range of 50° to 60° C. High-performance liquid chromatography (HPLC) was used to confirm the consumption of 1-methoxy-2-methylnaphthalene.

At the end of reaction, 200 ml of hot water (about 50° C. ) was added and the resulting mixture was extracted twice with 200 ml each isopropylether. To the combined extracts were added 200 ml of n-hexane and 5 g of activated charcoal, the mixture was stirred at 50° C. for 30 minutes, and the insoluble matters and activated charcoal were filtered off. The filtrate was dried over anhydrous magnesium sulfate and concentrated, giving 9.5 g (61.0%) of 2-methyl-1,4-naphthoquinone as yellow crystals. The purity was 98.8% when measured by HPLC (relative peak-area method; UV detection at 254 nm).

EXAMPLE 2

2-Methyl-1,4-naphthoquinone was prepared in much the same manner as in Example 1, except that 18.6 g of 1-ethoxy-2-methylnaphthalene (86% content) was used in place of 1-methoxy-2-methylnaphthalene and the amount of 35% hydrogen peroxide was increased to 36.0 g. The yield was 9.3 g (58.1%).

EXAMPLE 3

2-Methyl-1,4-naphthoquinone was prepared in much the same manner as in Example 1, except that no water was used. The yield was 8.6 g (55.6%).

EXAMPLE 4

2-Methyl-1,4-naphthoquinone was prepared in much the same manner as in Example 1, except that the amounts of water and glacial acetic acid were increased to 20 ml and 200 ml, respectively. The yield was 9.4 g (60.7%).

EXAMPLE 5

2-Methyl-1,4-naphthoquinone was prepared in much the same manner as in Example 1, except that the amount of potassium ferricyanide was decreased to 0.1 g. The yield was 8.8 g (58.1%).

EXAMPLE 6

2-Methyl-1,4-naphthoquinone was prepared in much the same manner as in Example 1, except that potassium ferrocyanide (0.5 g) was used in placed of potassium ferricyanide. The yield was 9.2 g (59.4%).

What is claimed is:

1. A process for producing 2-methyl-1,4-naphthoquinone which comprises reaction of a 1-lower-alkoxy-2-methyl-naphthalene with hydrogen peroxide in a solvent at a temperature of 20°–100° in the presence of a hexacyanoferric acid or its alkali metal or ammonium salt thereof as catalyst.

2. The process for producing 2-methyl-1,4-naphthoquinone as defined in claim 1, wherein said 1-lower-alkoxy-2-methylnaphthalene is 1-methoxy-2-methyl-naphthalene or 1-ethoxy-2-methylnaphthalene.

3. The process for producing 2-methyl-1,4-naphthoquinone as defined in claim 1, wherein the salt is an alkali metal hexacyanoferrate.

4. The process for producing 2-methyl-1,4-naphthoquinone as defined in claim 3, wherein said alkali metal hexacyanoferrate catalyst is potassium hexacyanoferrate(III), potassium ferricyanide, or potassium hexacyanoferrate(II), potassium ferrocyanide.

5. The process for producing 2-methyl-1,4-naphthoquinone as defined in claim 1, wherein said solvent is glacial acetic acid or an aqueous acetic acid.

6. The process for producing 2-methyl-1,4-naphthoquinone as defined in claim 1, wherein said reaction is carried out at a temperature in the range from 20° to 80° C.

* * * * *